United States Patent [19]

Kim et al.

[11] Patent Number: 5,010,089

[45] Date of Patent: Apr. 23, 1991

[54] CCK ANTAGONISTS AND THEIR USE IN TREATING GASTROINTESTINAL DISORDERS

[75] Inventors: Sun H. Kim, Chestnut Hill; Sylviane Moreau, Upton, both of Mass.

[73] Assignee: Biomeasure, Inc., Hopkinton, Mass.

[21] Appl. No.: 396,567

[22] Filed: Aug. 21, 1989

Related U.S. Application Data

[63] Continuation-in-part of Ser. No. 231,493, Aug. 12, 1988, abandoned, which is a continuation-in-part of Ser. No. 815,217, Dec. 31, 1985, Pat. No. 4,814,463.

[51] Int. Cl.$^5$ ................. C07D 209/18; C07D 403/12; A61K 31/405; A61K 31/47
[52] U.S. Cl. ............................ 514/314; 546/169; 548/495
[58] Field of Search ............ 548/495; 546/169; 514/314, 419

[56] References Cited

U.S. PATENT DOCUMENTS 4,803,284  2/1989  Morales-Rios et al. ............ 548/495
4,814,463  3/1989  Kim ................................... 548/495

FOREIGN PATENT DOCUMENTS 0106281  4/1984  European Pat. Off. .
0224151  6/1987  European Pat. Off. .
0230151  7/1987  European Pat. Off. .

*Primary Examiner*—David B. Springer
*Attorney, Agent, or Firm*—Fish & Richardson

[57] ABSTRACT

In general, the invention features compounds having the formula:

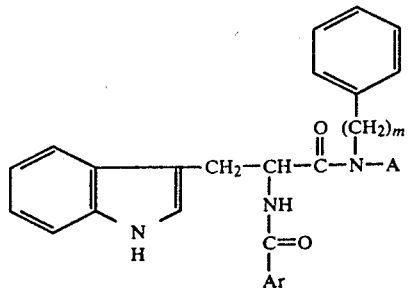

or a pharmaceutically acceptable salt thereof, wherein AR is an indolyl, quinolyl, naphthyl or a mono- or di-$R^1$ substituted naphthyl in which $R^1$ is, independently, an alkyl group having 1-5, inclusive, carbon atoms, an alkoxy group having 1-5, inclusive, carbon atoms, a halogen, amino, hydroxy, nitro, cyano, carboxyl, trifluoromethyl, ethyl carboxylate, or a hydrogen; m is an integer between 0 and 2, inclusive; and A is either

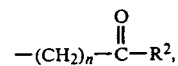

where n is an integer between 1 and 5, inclusive, and $R^2$ is hydroxy, an alkoxy group having 1-5, inclusive, carbon atoms, aralkoxy, aralkyl, amino, an alkyl group having 1-5, inclusive, carbon atoms, an alkylamino group having 1-5, inclusive, carbon atoms, a dialkylamino group with each alkyl group, independently, having 1-5, inclusive, carbon atoms, an N-heterocyclic group wherein the ring has 4-6, inclusive, atoms; or A is an alkyl group having 1-5, inclusive, carbon atoms, a hydroxyalkyl group having 1-5, inclusive, carbon atoms, an alkoxyalkyl group having 2-8, inclusive, carbon atoms, an aralkoxyalkyl having 8-14, inclusive, carbon atoms, an aryl group having 6-14, inclusive, carbon atoms, an aralkyl group having 6-14, inclusive, carbon atoms, or a cycloalkyl group having 3-12, inclusive, carbon atoms.

12 Claims, No Drawings

CCK ANTAGONISTS AND THEIR USE IN TREATING GASTROINTESTINAL DISORDERS

BACKGROUND OF THE INVENTION

This application is a continuation-in part of Kim U.S patent application Ser. No. 231,493, filed Aug. 12, 1988, abandoned, which is a continuation in part of Kim U.S. patent application Ser. No. 815,217, filed Dec. 31, 1985 from which U.S. Pat. No. 4,814,463 issued on Mar. 21, 1989.

This invention relates to cholecystokinin (CCK) antagonists.

Chang et al., 230 Science 177 (1985), describes CCK as "a hormonal regulator of pancreatic and gastric secretion, contraction of the gallbladder, and put motility," and states that "CCK also exists in the brain and may have an equally important role as a central nervous system transmitter." Chang et al. further mentions that CCK antagonists have "potential therapeutic utilities" and describes the compound asperlicin, which has the structure

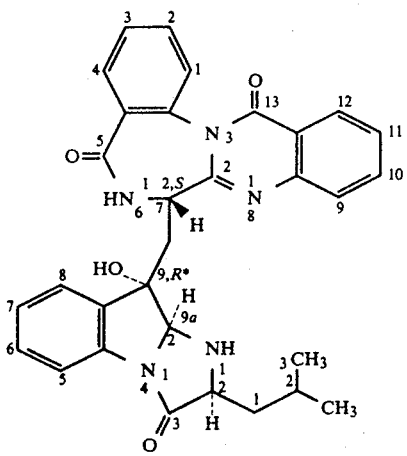

, as a CCK antagonist.

Rovati et al., U.S. Pat. No. 4,000,297, discloses compounds of the structure

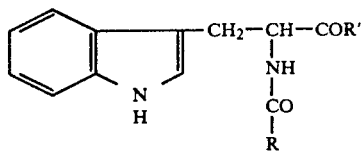

in which R includes mono and poly substituted phenyl groups, and $R^1$ includes hydroxyl, an aniline group substituted at the para position with a carboxylic acid or ester thereof, an amino group substituted with phenylacetic acid or ester derivative thereof, or an alkoxy group terminating with an amino group. The compounds are described as having an antispastic effect on the smoother muscle of the gastroenteric tract, as regulating gastric secretion, and as being protective of gastroenteric mucosa.

SUMMARY OF THE INVENTION

In general, the invention features compounds having the formula:

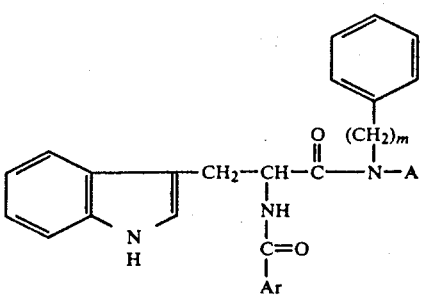

or a pharmaceutically acceptable salt thereof, wherein AR is an indolyl, quinolyl, naphthyl or a mono- or di-$R^1$ substituted naphthyl in which $R^1$ is, independently, an alkyl group having 1-5, inclusive, carbon atoms, an alkoxy group having 1-5, inclusive, carbon atoms, a halogen, amino, hydroxy, nitro, cyano, carboxyl, trifluoromethyl, ethyl carboxylate, or a hydrogen; m is an integer between 0 and 2, inclusive; and A is either

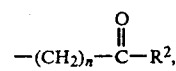

where n is an integer between 1 and 5, inclusive, and $R^2$ is hydroxy, an alkoxy group having 1 to 5, inclusive, carbon atoms, aralkoxy (e.g., benzyloxy), aralkyl (e.g., benzyl), amino, an alkyl group having 1 to 5, inclusive, carbon atoms, an alkylamino group having 1 to 5, inclusive, carbon atoms, a dialkylamino group with each alkyl group, independently, having 1 to 5, inclusive, carbon atoms, an N-heterocyclic group wherein the ring has 4 to 6, inclusive, atoms (e.g., pyrrolidino, piperidino, N-methylpiperazino, or morpholino); or A is an alkyl group having 1 to 5, inclusive, carbon atoms, a hydroxyalkyl group having 1 to 5, inclusive, carbon atoms, an alkoxyalkyl group having 2 to 8, inclusive, carbon atoms, an aralkoxyalkyl group having 8 to 14, inclusive, carbon atoms, an aryl group (e.g., phenyl, toluyl) having 6 to 14, inclusive, carbon atoms, an aralkyl group (e.g., benzyl, phenylethyl) having 6 to 14, inclusive, carbon atoms, or a cycloalkyl group having 3 to 12, inclusive, carbon atoms In preferred embodiments of the invention, the tryptophan residue is of the L-configuration or the D-configuration, m is 2, and $R^2$ is an alkoxy group or hydroxy. Preferred compounds include α-N-(2-indolylcarbonyl)-L-tryptyl-N'-phenylethylglycine, α-N (2-indolylcarbonyl)-D-tryptyl-N'-phenylethylglycine, α-N-(2-indolylcarbonyl)-L-tryptyl-N'-phenylethylglycine-ethylester, α-N-(2 quinolylcarbonyl) L-tryptyl-N'-phenylethylglycine, α-N-(3-quinolylcarbonyl) L-tryptyl N'-phenylethylglycine, α-N (2 naphthylcarbonyl)-L-tryptyl-N'-phenylethylglycine, or a pharmaceutically acceptable salt thereof.

In other preferred embodiments, a therapeutically effective amount of the therapeutic compound and a pharmaceutically acceptable carrier substance, e.g., magnesium carbonate or lactose, form a therapeutic composition, e.g., a pill, tablet, capsule, or liquid, for oral administration to a patient; a liquid or an ointment capable of being administered transdermally, nasally, rectally, or sublingually; a liquid capable of being administered intravenously, parenterally, subcutaneously, or intraperitoneally; or an oral or a parenteral sustained release formulation. An example of a liquid formulation for oral administration comprises a therapeutic amount of the compound of the invention, and polyethylene glycol 400, propylene glycol and water, in ratios adjusted for solubility.

The compounds of the invention are effective cholecystokinin antagonists and as such are effective in treating and preventing disorders involving CCK. Examples of such disorders include gastrointestinal disorders, for example, involving gastrointestinal motility, e.g., gastroesophageal reflux, gastritis, gastroparesis, biliary dyskenesia, irritable bowel syndrome, acute obstructive cholecystitis, or colitis; or involving colon motility; or involving pancreatic and/or gastric secretion, e.g., acute or chronic pancreatitis, hyperinsulinemia, or Zollinger-Ellison syndrome; antral G cell hyperplasia; or central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; or pain (potentiation of opiate analgesia). They are also effective, alone or in combination with other chemotherapeutic agents, in the treatment of autoproliferative disorders, such as pancreatic cancer or hyperplasia; this activity is believed to occur because of antagonism to the action of cholecystokinin in inducing pancreatic hyperplasia in the presence of known carcinogens, e.g., nitrosamine. The compounds are stable, inexpensive to make, and non-toxic.

Other features and advantages of the invention will be apparent from the following description of the preferred embodiments thereof, and from the claims.

DESCRIPTION OF THE PREFERRED EMBODIMENTS

We now describe the structure, synthesis, and use of preferred embodiments of the invention.

Structure

The compounds of the invention have the general formula recited in the summary of the invention above. Examples of preferred compounds within this formula are those referred to as preferred embodiments above.

The compounds of the invention are N substituted (D- or L-) tryptyl N'-disubstituted glycine or N-substituted (D- or L-) tryptyl N'-disubstituted amide derivatives. The compounds of the invention include all stereoisomers of the compounds.

The compounds can also be provided in the form of pharmaceutically acceptable salts. Examples of suitable salts include those formed with hydrochloric, hydrobromic, sulfuric, maleic, acetic, or fumaric acid; potassium, sodium, magnesium, calcium or aluminum hydroxide; or dicyclohexylamine.

Synthesis

The above compounds can be synthesized as follows. First, a compound of formula (2)

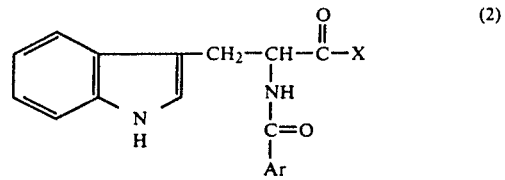

, where X represents a hydroxyl or carboxylic acid activating group, e.g., a halogen such as chlorine, and AR is defined as above, is condensed with a secondary amino compound of formula

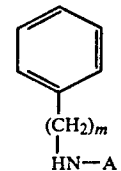

, where m and A are defined as before.

The corresponding acids are then prepared from these esters by hydrolyzing the esters with aqueous base. Amides can be prepared by treating the corresponding esters with ammonia or an amine.

Compounds within formulae (2) and (3) are commercially available; alternatively they can be synthesized according to standard methods, e.g., as described in Greenstein, et al, *Chemistry of the Amino Acids,* Vols. 1-3, J. Wiley, New York (1961); *J. Pharm. Sci.,* 51: 1058 (1962); *Org. Reaction,* 5: 301 (1949); *J. Chem. Soc.* (c), 2223 (1969); and *J. Org. Chem.:* 37, 1673 (1972).

The condensation reactions are preferably carried out in an inert organic solvent, e.g., dimethylformamide, dichloromethane, tetrahydrofuran, benzene, or acetonitrile, using a suitable mild condensing agent, e.g., thionylchloride, oxalylchloride, or dicyclohexylcarbodiimide (DCC), and optionally a catalyst, e.g., 1-hydroxybenzotriazole (HOBT). The reaction temperature is maintained below room temperature ($-15°$ C. to room temperature) in order to minimize side reactions. Typical condensation procedures are described in Schroeder et al., *The Peptides,* Vols. 1-2 (1965. 1966) and Gross et al., *The Peptides,* Vols. 1-3 (1979, 1980, 1981).

The intermediate and final products are isolated and purified by standard methods e.g., column chromatography or crystallization. Purity is determined using chromatographic, spectroscopic, and chemical analysis.

Specific compounds are made as follows.

α-N-(2-Indolylcarbonyl)-L tryptyl-N'-phenylethylglycineethylester

The first step is the preparation of α-N-(2-indolylcarbonyl)-L-tryptophan, as follows. To an ice-cooled solution of L tryptophan methylester HCl (1.0 g), indole 2-carboxylic acid (0.63 g), and diethylcyanophosphonate (0.71 g) in 10 ml dimethylformamide is added dropwise 1.65 ml triethylamine, and the reaction mixture is stirred at 0.5° C. for 1 hour and then at room temperature overnight. Volatile substances are removed in vacuo, and the residue is partitioned between chloroform and water. Precipitate (1.2 g) is collected by filtration, washed with chloroform, and then dried. (TLC: silica gel; CHCl$_3$/MeOH=9:1; Rf=0.71.)

To a suspension of α-N-(2 indolylcarbonyl)-L-tryptophan methylester (1 g) in 20 ml ethanol is added 3 ml 1N NaOH, and after 1 hour stirring at room temperature, solvent is removed in vacuo to a small volume (~5 ml). The resulting solution is diluted with water and acidified with dilute HCl to pH 2–3. Pale pink solid (950 mg) is collected by filtration, washed with water, and then dried. (TLC: silica gel; CHCl$_3$/MeOH/HOAC=9:1:0.1; Rf=0.32.)

The acid is then condensed with the N'-phenylethyl substituted ethyl ester of glycine, as follows. To a solution of 1.25 ml phenylethylamine in 10 ml chloroform is added with stirring 0.56 ml ethylobromoacetate. After two hours, the precipitate is filtered off and the solvent is removed in vacuo to dryness. The residue is subsequently triturated with ether, the precipitate is filtered off and the filtrate is concentrated in vacuo to give 1.0 g product as an oil. (TLC: silica gel.; CHCl$_3$/acetone=9:1; Rf=0.29.)

To an ice-cooled solution of α-N-(2-indolylcarbonyl)-L-tryptophan (0.8 g), 1-hydroxybenzotriazole (0.65 g) and N-phenylethylglycine-ethylester (0.51 g) in dimethylformamide-dichloromethane (1:1, 20 ml) is added a cold solution of dicyclohexylcarbodiimide (0.55 g) in 1 ml dichloromethane. The mixture is stirred at 0.5° C. for 1 hour and then at room temperature overnight.

The mixture is then filtered, and solvents are evaporated in vacuo to dryness. The residue is dissolved in chloroform, washed with 5% aqueous NaHCO$_3$ and water, and dried over anhydrous MgSO$_4$. After evaporation of solvent, the residue is chromatographed on silica gel (45 g) using chloroform-acetone (9:1) as eluant. Appropriate fractions are pooled and the solvent removed in vacuo to dryness. The pale yellow solid is recrystallized from ethanol to form a colorless solid (0.44 g). (TLC: silica gel; CHCl$_3$/acetone=9:1; Rf=0.34.)

α-N-(2-indolylcarbonyl) L-tryptyl N'-phenylethylglycine

To a suspension of α-N-(2-indolylcarbonyl)-L-tryptyl-N'-phenylethylglycine ethylester (200 mg) in 2 ml ethanol is added 1 ml 2N NaOH. After 1 hour stirring at room temperature, most of the ethanol is removed in vacuo. The solution is then acidified with dilute HCl to pH 2–3. Colorless solid (130 mg) is collected by filtration, washed with water, and then dried. (TLC: silica gel; CHCl$_3$/MeOH/HOAC=9:1:0.1; Rf=0.55.)

Additional Compounds

Additional compounds of the invention may be synthesized in an analagous manner. Data obtained for some of these additional compounds is as follows:

α-N-(3-quinolylcarbonyl)-L-tryptyl-N'-phenylethylglycine (TLC: silica gel, CHCl$_3$/MeOH/HOAC=6:1:0.3; Rf=0.61; Elemental analysis: experimental, C 68.34/H 5.58/N 10.44, calculated values for C$_{30}$ H$_{28}$ N$_4$ O$_4$, C 68.10/H 5.53/N 10.25);

α-N-(2-naphthylcarbonyl)-L tryptyl-N'-phenylethylglycine (TLC: silica gel, CHCl$_3$/MeOH/HOAC=9:1:0.2; RF=0.48; Elemental Analysis: experimental, C 72.06/H 5.66/N 7.63, calculated values for C$_{32}$ H$_{28}$ $_3$ O$_4$.½ H$_2$O, C 72.43/H 5.33/N 7.91); and α-N-(2-indolylcarbonyl)-D-tryptyl-N'-phenylethylglycine (TLC: silica gel, CHCl$_3$/MeOH/HOAC=9:1:0.2; Rf=0.48; Elemental analysis: experimental, C 69.33/H 5.65/ N 10.63, calculated values for C$_{30}$ H$_{28}$ N$_4$ O$_4$.½ H$_2$O, C 69.61/H 5.64/N 10.82).

The compounds of the invention are stable, inexpensive to make, and non-toxic.

Inhibition studies of CCK by specific compounds of the present invention were carried out as follows. Male, Sprague-Dawley rats were sacrificed by decapitation and the pancreas or cerebral was removed and homogenized with a Brinkman Polytron (setting 6, 15 sec). The homogenates were centrifuged twice at 39,000 g for 10 min (4° C.), with an intermediate resuspension in fresh buffer. The final pellets were resuspended in the following buffer for the [$^{125}$I]CCK8 binding assay: 10 mM HEPES, 118 mM NaCL, 4.7 mM KCl, and 5 mM MgCL$_2$, 1 mM EGTA, 5 mg/ml bovine serum albumin, and 0.25 mg/ml bacitracin.

For the [$^{125}$I]CCK8 binding assay, aliquots of the membrane preparations were added to plastic culture tubes containing 0.05 nM [$^{125}$I]CCK8 (2200 Ci/mmol, New England Nulclear Corp ) and various concentrations of the test compounds in a final volume of 0.5 ml. The incubation period was 90 min (25° C.). The binding reaction was terminated by the addition of 4 ml of ice-cold buffer, followed by filtration through Whatman GF/B filters which had been previously soaked in 2% bovine serum albumin. Each tube and filter were then washed three times with 4-ml aliquots of ice-cold buffer. The radioactivity trapped on the filters was counted in an LKB Clini Gamma counter. Specific binding was defined as the total [$^{125}$I]CCK8 bound minus that bound in the presence of 1 μM unlabeled CCK8.

Table 1 sets forth data from inhibition studies of CCK by specific compounds of the present invention in which Ar, m, and A are defined as set forth below:

TABLE 1

| Ar | m | A | Pancreatic CCK Receptor IC$_{50}$ (micromoles) |
| --- | --- | --- | --- |
| 2-quinolyl | 2 | CH$_2$CO$_2$H | 0.17 |
| 2-naphthyl | 2 | CH$_2$CO$_2$H | 0.5 |
| 2-indolyl (D-Trp) | 2 | CH$_2$CO$_2$H | 0.03 |

In vivo studies were made to test the therapeutic effect of α-N-(2-indolylcarbonyl) L-tryptyl-N'-phenylethylglycine (BIM-18216), α-N-(3-quinolylcarbonyl)-L-tryptyl-N'-phenylethylglycine (BIM-18225), α-N-(2-naphthylcarbonyl)-L-tryptyl-N'-phenylethylglycine (BIM-18226), and α-N-(2-indolylcarbonyl) D-tryptyl-N'-phenylethylglycine (BIM-18227). The effect of the foregoing compounds on gastric emptying was measured as the percentage of anti-spasmodic activity. Tests were carried out on female CF$_1$ mice as follows. Mice weighing approximately 20 g were fasted overnight. Test compounds were administered in one of four ways: intraperitoneally (i.p.), subcutaneously (s.c.), intravenously (i.v.), or orally (p.o.). Test compounds administered orally were dissolved in a mixture of 75% by volume polyethylene glycol 400 NF, 15% by volume propylene glycol USP, and 10% by volume purified H$_2$O USP. For other methods of administration, the test compounds were dissolved in a solution of saline containing 10% DMSO (by volume) for i.v. administration; and in a solution of saline containing 10% DMSO (by volume) and 0.25% methylcellulose (by weight) for s.c. or i.p. administration. Test compounds were administered to the mice 15 minutes prior to administering CCK-8 (40 μg/kg, s.c.). The mice were fed a charcoal meal orally 5 minutes after CCK injection and the animals were sacrificed 5 minutes later. The lengths of the intestines filled with charcoal were measured and the % of anti-spasmodic activity was calculated based upon the lengths according to the following formula:

$$\frac{\text{Length (Test Group)} - \text{Length (CCK Group)}}{\text{Length (Control Group)} - \text{Length (CCK Group)}} \times 100$$

Table 2, below, contains data on the anti-spasmodic activity of the compounds tested by oral administration.

TABLE 2

| Compound | Dose (mg/kg) | Route of Administration | % Anti-Spasmodic Activity |
|---|---|---|---|
| BIM-18216 | 125 | p.o. | 78 |
| BIM-18225 | 125 | p.o. | 22 |
| BIM-18226 | 125 | p.o. | 88 |
|  | 100 | p.o. | 35 |
| BIM-18227 | 125 | p.o. | 60 |
|  | 100 | p.o. | 24 |

Table 3, below, contains data for the test compound BIM-18216 administered in each of the four different ways discussed above.

TABLE 3

| Compound | Dose (mg/kg) | Route of Administration | % Anti-Spasmodic Activity | ED$_{50}$ |
|---|---|---|---|---|
| BIM-18216 | 25 | i.p. | 91 | 5.8 mg/kg |
|  | 5 | i.p. | 45 |  |
|  | 1 | i.p. | 1 |  |
|  | 50 | s.c. | 112 | 4.5 mg/kg |
|  | 25 | s.c. | 108 |  |
|  | 10 | s.c. | 75 |  |
|  | 5 | s.c. | 53 |  |
|  | 1 | s.c. | 1 |  |
|  | 25 | i.v. | 123 | 6.6 mg/kg |
|  | 10 | i.v. | 70 |  |
|  | 5 | i.v. | 36 |  |
|  | 500 | p.o. | 105 | 96.7 mg/kg |
|  | 250 | p.o. | 88 |  |
|  | 125 | p.o. | 81 |  |
|  | 100 | p.o. | 56 |  |
|  | 75 | p.o. | 47 |  |
|  | 50 | p.o. | 10 |  |

Use

When administered to a patient (e.g., orally, intravenously, parenterally, nasally, or by suppository), the compounds are effective cholecystokinin antagonists and as such are effective in treating and preventing disorders involving CCK. Examples of such disorders include gastrointestinal disorders, for example, involving gastrointestinal motility, e.g., gastroesophageal reflux, gastritis, gastroparesis, biliary dyskenesia, irritable bowel syndrome, acute obstructive cholecystitis, or colitis; or involving colon motility; or involving pancreatic and/or gastric secretion, e.g., acute or chronic pancreatitis, hyperinsulinemia, or Zollinger-Ellison syndrome; antral G cell hyperplasia; or central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; or pain (potentiation of opiate analgesia). They are also effective, alone or in combination with other chemotherapeutic agents, in the treatment of autoproliferative disorders, such as pancreatic cancer or hyperplasia; this activity is believed to occur because of antagonism to the action of cholecystokinin in inducing pancreatic hyperplasia in the presence of known carcinogens, e.g., nitrosamine.

The compounds can be administered to a human patient in a dosage of 0.1–50mg/kg/day, preferably about 0.1 mg/kg/day when administered parenterally and about 50 mg/kg/day when administered orally.

Other embodiments are within the following claims.

We claim:

1. A compound having the formula

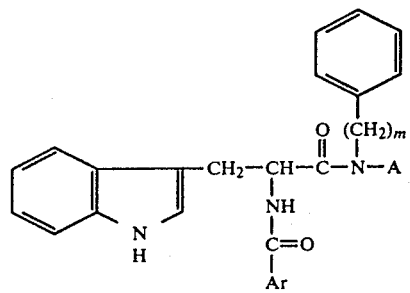

or pharmaceutically acceptable salt thereof,
wherein Ar is an indolyl, quinolyl or naphthyl;
m is an integer between 0 and 2, inclusive; and
A is either

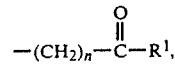

wherein n is an integer between 1 and 5, inclusive, and R$^2$ is hydroxy, an alkoxy group having 1–5, inclusive, carbon atoms, or aralkoxy.

2. The compound of claim 1 wherein the tryptophan residue is of the L-configuration, Ar is 2-indolyl, m is 2, and A is

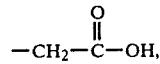

said compound having the name α-N-(2-indolylcarbonyl)-L-tryptyl-N'-phenylethylglycine; or a pharmaceutically acceptable salt thereof.

3. The compound of claim 1 wherein the tryptophan residue is of the D-configuration, Ar is 2-indolyl, m is 2, and A is

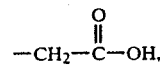

said compound having the name α-N-(2-indolylcarbonyl)-D-tryptyl N'-phenylethylglycine; or a pharmaceutically acceptable salt thereof.

4. The compound of claim 1 wherein the tryptophan residue is of the L configuration, Ar is 2-indolyl, m is 2, and A is

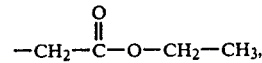

said compound having the name α-N-(2-indolylcarbonyl)-L-tryptyl-N'-phenylethylglycineethylester; or a pharmaceutically acceptable salt thereof.

5. The compound of claim 1 wherein the tryptophan residue is of the L-configuration, Ar is 2-quinolyl, m is 2, and A is

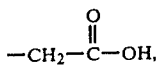

said compound having the name α-N-(2-quinolylcarbonyl)-L-tryptyl-N'-phenylethylglycine; or a pharmaceutically acceptable salt thereof.

6. The compound of claim 1 wherein the tryptophan residue is of the L configuration, Ar is 3-quinolyl, m is 2, and A is

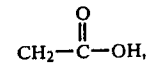

said compound having the name α-N-(3-quinolylcarbonyl)-L-tryptyl-N'-phenylethylglycine; or a pharmaceutically acceptable salt thereof.

7. The compound of claim 1 wherein the tryptophan residue is of the L-configuration, Ar is 2-naphthyl, m is 2, and A is

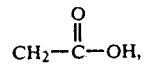

said compound having the name α-N-(2-naphthylcarbonyl)-L-tryptyl-N'-phenylethylglycine; or a pharmaceutically acceptable salt thereof.

8. The compound of claim 1 wherein m is 2.

9. The compound of claim 1 wherein A is

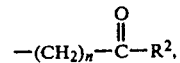

wherein $R^2$ is hydroxy or an alkoxy group having 1-5, inclusive, carbon atoms.

10. The compound of claim 1 wherein m is 1.

11. A method for preventing a patient having excessive cholecystokinin from developing a gastrointestinal disorder comprising administering to the patient an effective amount of the compound of any of claim 1-10.

12. The method of claim 11 wherein said gastrointestinal disorder is a gastric motility disorder or a colon motility disorder.

* * * * *

UNITED STATES PATENT AND TRADEMARK OFFICE
CERTIFICATE OF CORRECTION

PATENT NO. : 5,010,089

DATED : April 23, 1991

INVENTOR(S) : Sun H. Kim, and Sylviane Moreau

It is certified that error appears in the above-identified patent and that said Letters Patent is hereby corrected as shown below:

Column 5, line 52, "analogous" is misspelled.

Signed and Sealed this

Twenty-fifth Day of May, 1993

Attest:

MICHAEL K. KIRK

Attesting Officer     Acting Commissioner of Patents and Trademarks